United States Patent [19]

Nakatani et al.

[11] 4,157,333
[45] Jun. 5, 1979

[54] PROCESS FOR PREPARING PIPERONAL

[75] Inventors: Kiyoshi Nakatani, Tokyo; Tsuneo Inoue, Yokohama; Tutomu Nishizawa, Kamakura; Satoshi Numata, Yokohama; Tsutomu Ishii, Kawasaki, all of Japan

[73] Assignee: Mitsui Toatsu Chemicals, Inc., Tokyo, Japan

[21] Appl. No.: 862,392

[22] Filed: Dec. 20, 1977

[51] Int. Cl.$^2$ ............................................. C07D 317/44
[52] U.S. Cl. ............................................. 260/340.5 R
[58] Field of Search ................................. 260/340.5 R

[56] References Cited
PUBLICATIONS

Chem. Abstracts 68:114284e.
Chem. Abstracts 85:94067g.
"Excerpts of Lectures given at the 21st Forum on Aromatics, Terpenes and Essential Oil Chemistry on Nov. 3–5, 1977 at the Tokushima University, Japan.

Primary Examiner—Ethel G. Love

[57] ABSTRACT

A process for preparing piperonal which comprises the steps of reacting 1,2-methylenedioxybenzene with an N-alkylformanilide and a condensing agent comprising one or more compounds selected from the group consisting of phosgene, phosphorus oxychloride, phosphorus oxybromide, thionyl chloride, thionyl bromide, sulfuryl chloride, sulfuryl bromide, phosphorus trichloride, and phosphorus pentachloride, and then hydrolyzing the resulting reaction product.

17 Claims, No Drawings

PROCESS FOR PREPARING PIPERONAL

BACKGROUND OF THE INVENTION

This invention relates to a novel process for preparing piperonal.

Piperonal is the basis of heliotrope type perfume compositions and is widely used in perfumes for general cosmetic preparations. In addition, it is very useful as an industrial material for the production of drugs, agricultural chemicals, and the like and as a brightener for metal plating. Industrially, piperonal is now being produced mainly by isolating safrole from the essential oil of Ocotea cymbarum and oxidizing it with ozone or dichromate. In recent years, however, the tendency toward the exhaustion of natural resources from which safrole can be obtained has created a growing demand for stable supply of piperonal through its industrial synthesis from petroleum chemicals.

Conventional processes for preparing piperonal can be divided into two groups: one starting with 1,2-methylenedioxybenzene prepared from pyrocatechol and the other starting with 3,4-dihydroxybenzaldehyde. The former is found to be more advantageous to industrial applications.

Several processes for preparing piperonal from 3,4-dihydroxybenzaldehyde are known.

(1) In order to prepare the starting material or 3,4-dihydroxybenzaldehyde, a process has been proposed which involves condensing pyrocatechol with glyoxylic acid in aqueous alkali and then oxidizing the resulting dihydroxymandelic acid (Japanese Patent Application Disclosure No. 2,952/'75). The yield attainable with this process is at most 77%.

(2) One process for preparing piperonal from 3,4-dihydroxybenzaldehyde comprises reacting 3,4-dihydroxybenzaldehyde with methylene chloride and alkali in a non-protic polar solvent such as dimethyl sulfoxide, and gives a 61% yield of piperonal (British Pat. No. 1,097,270). Another process comprises reacting 3,4-dihydroxybenzaldehyde with methylene chloride in aqueous alkali under the influence of an interphasic moving catalyst such as quaternary ammonium compound, and gives a 70-73% yield of piperonal. However, the catalyst used in this process is expensive and, by nature, easily soluble in both aqueous and organic phases. Accordingly, the recovery of the catalyst is too low to make this process practicable (Japanese Patent Application Disclosure Nos. 23,265/'76 and 113,967/'77). In any event, neither of these process can provide satisfactory yields based on the amount of the starting material. In addition, James H. Clark et al. have described still another process in which 3,4-dihydroxybenzaldehyde is reacted with dibromomethane in N,N-dimethylformamide under the influence of an excess of potassium fluoride or cesium fluoride to give a 90% yield of piperonal [Tetrahedron Letters, No. 38, pp. 3361-3364 (1976)]. This process is of advantage in that no strong base is used, the reaction time is relatively short, and a high yield can be obtained. However, an expensive fluoride must be used in large excess as a halogen trapping agent and cannot be recycled because its fluorine component is stoichiometrically replaced by the halogen atoms in the dihalomethane used. Accordingly, this process is not satisfactory for industrial applications. Moreover, when based on the amount of pyrocatechol used, the yield attainable with this process does not reach 70%.

Meanwhile, several processes for preparing piperonal from 1,2-methylenedioxybenzene are also known.

(1) The starting material or 1,2-methylenedioxybenzene can be prepared by processes in which pyrocatechol is reacted with methylene chloride and alkali in a non-protic polar solvent such as dimethyl sulfone to give a 91-99% yield (British Pat. No. 1,097,270 and Japanese Patent Application Disclosure Nos. 5,963/'76 and 13,773/'76). In addition, other processes which can give high yields of 1,2-methylenedioxybenzene are also available. Accordingly, it would be of great advantage from an industrial viewpoint if piperonal could be prepared from 1,2-methylenedioxybenzene with good yield and high selectivity.

(2) A typical process for preparing piperonal from 1,2-methylenedioxybenzene has been reported by P. P. Shorygin et al. [J. Gen. Chem. (U.S.S.R.), 8,975 (1938)]. This is a two-step process. In the first step, 1,2-methylenedioxybenzene is reacted with formalin in petroleum benzine under the influence of hydrogen chloride gas and zinc chloride to form piperonyl chloride (with a 70-78% yield based on the amount of 1,2-methylenedioxybenzene having reacted). This is followed by the second step in which the piperonyl chloride is reacted with an equimolar amount of hexamine in 60% alcohol to give a 70-80% yield of piperonal. By E. D. Laskina et al. [Chemical Abstracts, 57,9714 (1962)], another process has been described in which 1,2-methelenedioxybenzene is reacted with formalin in the presence of a large excess of the sodium salt of m-nitrobenzenesulfonic acid, hydrogen chloride, and an aluminum catalyst to give a 42.4% yield of piperonal.

However, these conventional processes are not entirely satisfactory for industrial applications because the yield and particularly selectivity (that is, the yield of piperonal based on the amount of 1,2-methylenedioxybenzene having reacted) is rather limited due to the abundant formation of tarry by-products, the procedure for reaction is complicated, and the large amount of metal hydroxide formed as a by-product must be disposed of.

SUMMARY OF THE INVENTION

It is, therefore, an object of this invention to provide an easily practicable process for preparing piperonal from 1,2-methylenedioxybenzene with good yield and particularly high selectivity based on the amount of the starting material.

As a result of intensive search for an easily practicable process which will eliminate the disadvantages of conventional processes and can give a high yield of piperonal, we have now found that piperonal can be obtained with good yield and high selectivity by reacting 1,2-methylenedioxybenzene with an N-alkylformanilide and a condensing agent comprising one or more compounds selected from the group consisting of phosgene, phosphorus oxychloride, phosphorus oxybromide, thionyl chloride, thionyl bromide, sulfuryl chloride, sulfuryl bromide, phosphorus trichloride, and phosphorus pentachloride, and then hydrolyzing the resulting reaction product. That is, this invention is based on the discovery that N-alkylformanilides can formylate 1,2-methylenedioxybenzene to produce piperonal with good yield and high selectivity, as contrasted with dimethylformamide which is commonly used as a formylating agent in the Vilsmeier reaction but found to give only a very low yield and selectivity of piperonal.

By the process of the invention, the desired product or piperonal is produced with good yield and high selectivity, as represented by the following reaction formula.

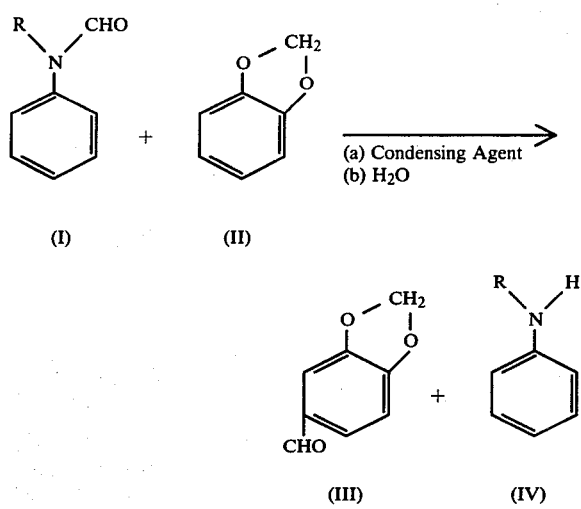

where the condensing agent (a) comprises one or more compounds selected from the group consisting of phosgene, phosphorus oxychloride, phosphorus oxybromide, thionyl chloride, thionyl bromide, sulfuryl chloride, sulfuryl bromide, phosphorus trichloride, and phosphorus pentachloride.

That is, 1,2-methylenedioxybenzene (II) is reacted with an N-alkylformanilide (I) and a condensing agent (a), such as phosgene or phosphorus oxychloride, and the resulting reaction product is then hydrolyzed to form piperonal (III) and an N-alkylaniline (IV).

The process of the invention is more preferably practiced by reacting an N-alkylformanilide (I) with a condensing agent (a), such as phosgene or phosphorus oxychloride, to form an addition product (hereinafter referred to as "amide chloride"), reacting the amide chloride with 1,2-methylenedioxybenzene (II), and then hydrolyzing the resulting reaction product.

In addition, the process of the invention facilitates the recovery of the N-alkylaniline (IV) formed along with piperonal (III). The N-alkylaniline thus obtained may be reacted with formic acid to form an N-alkylformanilide (I) which can then be recycled in the process of the invention. This also makes the process of the invention advantageous to industrial applications.

DETAILED DESCRIPTION OF THE INVENTION

Briefly stated, this invention provides a process for preparing piperonal which comprises the steps of reacting 1,2-methylenedioxybenzene with an N-alkylformanilide and a condensing agent comprising one or more compounds selected from the group consisting of phosgene, phosphorus oxychloride, phosphorus oxybromide, thionyl chloride, thionyl bromide, sulfuryl chloride, sulfuryl bromide, phosphorus trichloride, and phosphorus pentachloride, and then hydrolyzing the resulting reaction product.

The N-alkylformanilides which can be used in the practice of the invention are represented by the general formula

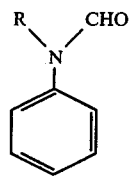

where R is an alkyl group having from 1 to 4 carbon atoms. Typical examples of these compounds are N-methylformanilide, N-ethylformanilide, N-isopropylformanilide, N-(n-propyl)formanilide, N-(n-butyl)formanilide, N-isobutylformanilide, N-(sec-butyl)formanilide, and N-(tert-butyl)formanilide. Among them, N-methylformanilide and N-ethylformanilide are most preferred. 1,2-Methylenedioxybenzene may be used in any desired proportion. From a practical viewpoint, however, it is desirable to use from 0.1 to 15 moles and preferably from 0.3 to 10 moles of 1,2-methylenedioxybenzene per mole of the N-alkylformanilide. It is also desirable to use from 0.3 to 5 moles and preferably from 0.7 to 2 moles of a condensing agent, such as phosgene or phosphorus oxychloride, per mole of the N-alkylformanilide.

The invention will be better understood from the following detailed description of preferred embodiments thereof.

In one preferred embodiment of the invention, an N-alkylformanilide is reacted with a condensing agent, such as phosgene or phosphorus oxychloride, to form an addition product which is hereinafter referred to as "amide chloride." This amide chloride is added to 1,2-methylenedioxybenzene kept at the reaction temperature. After the reaction mixture is allowed to stand, the resulting reaction product is hydrolyzed. More specifically, a condensing agent, such as phosgene or phosphorus oxychloride, is introduced into an N-alkylformanilide with effective stirring to form an amide chloride. This amide chloride is an intermediate product which serves to introduce an aldehyde group into the molecule of 1,2-methylenedioxybenzene. Although the above-described reaction may be carried out in the absence of any solvent, it is preferred to use 1,2-methylenedioxybenzene or an inert organic solvent as the solvent for reaction. When no solvent is used, the resulting amide chloride may be utilized either as it is or as a solution in 1,2-methylenedioxybenzene or an inert organic solvent. The amide chloride or a solution thereof is kept in that temperature range which allows it to remain in solution, and then continuously or intermittently added with effective stirring to 1,2-methylenedioxybenzene (or a mixture of 1,2-methylenedioxybenzene and an inert organic solvent) heated previously to a temperature at which it reacts with the amide chloride. Thus, the reaction of 1,2-methylenedioxybenzene with the amide chloride can be preferentially accomplished while the reaction between amide chloride molecules is suppressed. Thereafter, the resulting reaction product is hydrolyzed to obtain the desired final product or piperonal.

In this embodiment, the reaction for synthesis of an amide chloride is characterized as follows:

(1) No particular limitation is imposed on the reaction temperature, so long as it is lower than the level at which decomposition or polymerization takes place. However, for the purpose of suppressing the reaction between molecules of the amide chloride formed, it is desirable to use those temperatures which lie in the range of −40° to 100° C. and preferably −20° to 70° C. and allow the reacting mass to remain in solution.

(2) A condensing agent, such as phosgene or phosphorus oxychloride, is desirably introduced over a period of time as short as possible, but may be introduced over a long period of time if lower temperatures are used. Practically, it may vary from 5 minutes to 15 hours and preferably from 10 minutes to 5 hours.

(3) The reaction is usually carried out under atmospheric pressure, though subatmospheric and superatmospheric pressures may be used.

(4) However, when the condensing agent comprises thionyl chloride, thionyl bromide, sulfuryl chloride, or sulfuryl bromide, the reaction with an N-alkylformanilide is desirably carried out under reduced pressure, particularly under a pressure in the range of 20 to 400 mmHg, and at a temperature in the range of 0° to 80° C. and preferably 40° to 60° C. Moreover, it is preferred to carry out the reaction in the absence of any solvent, though 1,2-methylenedioxybenzene and/or inert organic solvent may be used as the solvent for reaction.

The amide chloride thus obtained or a solution thereof is kept at a temperature in the range of −40° to 60° C. and preferably −20° to 50° C.

The reaction of the amide chloride with 1,2-methylenedioxybenzene is carried out by adding the amide chloride or a solution thereof to 1,2-methylenedioxybenzene at a temperature in the range of 50° to 120° C. and preferably 60° to 100° C. over a period of time varying from 5 minutes to 15 hours and preferably from 10 minutes to 10 hours and then heating the reaction mixture at that temperature for a period of time varying from 5 minutes to 10 hours and preferably from 10 minutes to 3 hours. The resulting reaction product may be hydrolyzed, either directly or after cooling to room temperature, to form piperonal.

In another preferred embodiment of the invention, an N-alkylformanilide, 1,2-methylenedioxybenzene, and a condensing agent, such as phosgene or phosphorus oxychloride, are charged into a single reactor and allowed to react. More specifically, a mixture of an N-alkylformanilide and 1,2-methylenedioxybenzene and, if desired, an inert organic solvent is formed. Then a condensing agent, such as phosgene or phosphorus oxychloride, is added to this mixture with effective stirring and allowed to react. In this embodiment, it is possible to add the condensing agent and carry out the reaction at an identical temperature in the range of 50° to 100° C. and preferably 60° to 80° C. However, in view of the yield of piperonal and the recovery of the N-alkylaniline formed as a by-product, the condensing agent is desirably added at a temperature in the range of −40° to 100° C. and preferably −20° to 70° C. so as to form preferentially the amide chloride which is the addition product of the N-alkylformanilide with the condensing agent and, thereafter, the main reaction is carried out at a temperature in the range of 50° to 110° C. and preferably 60° to 110° C. The reaction time may vary from 1 to 30 hours and preferably from 2 to 15 hours, including the time required for addition of the condensing agent which may vary from 5 minutes to 15 hours and preferably from 10 minutes to 10 hours. The reaction is usually carried out under atmospheric pressure, though subatmospheric and super-atmospheric pressures may be used. However, when the condensing agent comprises thionyl chloride, thionyl bromide, sulfuryl chloride, or sulfuryl bromide, the reaction is desirably carried out under reduced pressure, particularly under a pressure in the range of 20 to 400 mmHg.

In either of the above-described embodiments, the resulting reaction product may be treated by conventional procedure. For example, the reaction product is poured with effective stirring into water kept at a temperature in the range of 0° to 100° C. and preferably 0° to 80° C., and thereby hydrolyzed to form the desired final product or piperonal and an N-alkylaniline which can be recycled. The resulting mixture is directly extracted with a solvent such as benzene, toluene, chloroform, carbon tetrachloride, dichloroethylene, and the like. The remaining aqueous phase is neutralized with alkali and the N-alkylaniline thus liberated is extracted with a solvent as described above. Each of the extracts is distilled under reduced pressure by conventional procedure to obtain unreacted 1,2-methylenedioxybenzene, the desired final product or piperonal, unreacted N-alkylformanilide, and the by-product or N-alkylaniline. The crude piperonal obtained by distillation may be recrystallized from alcohol by conventional procedure to yield high-purity piperonal suitable for use in perfume compositions. The above-described hydrolysis may also be carried out by pouring the reaction product into an alkaline solution.

In view of the yield and selectivity of piperonal and the recovery of the by-product or N-alkylaniline, the most preferred embodiment of the invention is such that phosgene or phosphorus oxychloride is used as the condensing agent and the main reaction is carried out while the reaction between molecules of the amide chloride which is the addition product of the N-alkylformanilide with the condensing agent is suppressed.

The condensing agents which can be used in the practice of the invention include phosgene, phosphorus oxychloride, phosphorus oxybromide, thionyl chloride, thionyl bromide, sulfuryl chloride, sulfuryl bromide, phosphorus trichloride, and phosphorus pentachloride. From the viewpoint of yield and selectivity of piperonal, it is desirable to use phosgene or phosphorus oxychloride. In industrial applications, however, phosgene is preferred to phosphorus oxychloride. The reasons for this are that the weight of phosphorus oxychloride required in the practice of the invention is about 1.5 times as great as that of phosgene because the invention involves an equimolar reaction, that phosphorus oxychloride gives a slower reaction rate and a lower yield than phosgene, that phosphorus oxychloride requires about 2.5 times as much alkali as phosgene for the purpose of neutralizing the acid formed during hydrolysis, and that phosphorus oxychloride necessitates the disposal of waste water containing phosphorus compounds.

If desired, inert organic solvents may be used in the practice of the invention. Typical examples of these solvents are benzene, chlorobenzene, o-dichlobenzene, chloroform, carbon tetrachloride, methylene chloride, and 1,2-dichloroethane.

In order to further illustrate this invention, the following examples are given.

EXAMPLE 1

Into a mixture of 97.6 g (0.80 mole) of 1,2-methylenedioxybenzene and 108 g (0.80 mole) of N-methylformanilide was introduced 87.1 g (0.88 mole) of phosgene at 50° C. over a 1-hour period. Then, the mixture was cooled to 15° C. On the other hand, 29.3 g (0.24 mole) of 1,2-methylenedioxybenzene was charged into another reactor and kept at 90° C. The above mixture was added to this reactor over a 5-hour period. After completion of the addition, the reaction mixture was kept at 90° C. for 30 minutes, poured into ice water, and allowed to stand for 1 hour. Then, the resulting mixture was extracted with toluene. By vacuum distillation, the toluene was removed and the distillate at 84°–85° C./30 mmHg was then collected to recover 63.4 g (0.52 mole) of unreacted 1,2-methylenedioxybenzene. Subsequently, the distillate at 131°–134° C./10 mmHg was collected to obtain 76.8 g (0.512 mole) of piperonal having a purity of 99.5%. The yield (expressed in terms of mole percentage based on the amount of N-methylformanilide used) and selectivity (expressed in terms of mole percentage based on the amount of 1,2-methylenedioxybenzene having reacted) of piperonal were 64.0% and 98.5%, respectively. This product had a melting point of 37° C.

The results of analysis of the product by gas chromatography, NMR spectroscopy, mass spectrometry, and IR spectroscopy were in complete agreement with those of an authentic sample.

The aqueous phase remaining after the above-described extraction with toluene was alkalified by addition of sodium hydroxide and then extracted with toluene.

By vacuum distillation, the toluene was removed and the distillate at 111°–113° C./50 mmHg was then collected to recover 64.5 g (0.603 mole) of N-methylaniline. Its recovery was 75.4%. Subsequently, the distillate at 151°–153° C./50 mmHg was collected to recover 6.7 g (0.050 mole) of N-methylformanilide. Its recovery was 6.3%. The N-methylaniline thus recovered could be reacted with formic acid to form N-methylformanilide.

EXAMPLE 2

Into a mixture of 97.7 g (0.80 mole) of 1,2-methylenedioxybenzene and 108 g (0.80 mole) of N-methylformanilide was introduced 80.0 g (0.81 mole) of phosgene at 50° C. over a 1-hour period. Then, the reaction mixture was heated at 70° C. for 5 hours, poured into ice water, and allowed to stand for 1 hour. Thereafter, the resulting mixture was treated in the same manner as in Example 1 to obtain 48.0 g (0.393 mole) of 1,2-methylenedioxybenzene and 58.9 g (0.392 mole) of piperonal. The yield and selectivity of piperonal were 49.0% and 96.3%, respectively. The recoveries of N-methylaniline and N-methylformanilide were 64.2% and 2.3%, respectively.

CONTROL 1

The precedure of Example 2 was repeated, except that 58.5 g (0.80 mole) of dimethylformamide was used in place of the N-methylformanilide. As a result, the conversion of 1,2-methylenedioxybenzene was 2.5%. The yield and selectivity of piperonal were 0.4% and 16.2%, respectively.

CONTROL 2

The precedure of Example 2 was repeated, except that 58.5 g (0.80 mole) of dimethylformamide was used in place of the N-methylformanilide and that the phosgene was introduced at 85°–90° C. over a 40-minute period and the reaction mixture was then heated at 90° C. for 7.5 hours. As a result, the conversion of 1,2-methylenedioxybenzene was 12.5%. The yield and selectivity of piperonal were 4.1% and 33%, respectively.

EXAMPLE 3

The procedure of Example 1 was repeated, except that phosphorus oxychloride was used in place of the phosgene. The results obtained are summarized in Table I.

EXAMPLE 4

The procedure of Example 2 was repeated, except that N-ethylformanilide was used in place of the N-methylformanilide and that the phosgene was introduced at 60° C. instead of 50° C. The results obtained are summarized in Table I.

EXAMPLE 5

The procedure of Example 1 was repeated, except that N-isopropylformanilide was used in place of the N-methylformanilide and that 1,2-dichloroethane was used as the solvent for reaction in an amount equal to that of the N-isopropylformanilide and as the solvent for extraction in place of the toluene. The results obtained are summarized in Table I.

EXAMPLE 6

The procedure of Example 5 was repeated, except that N-(n-butyl)formanilide was used in place of the N-isopropylformanilide. The results obtained are summarized in Table I.

Table I

| Example | R Group in N-Alkyl-formanilide | Piperonal (mole %) | | Recovery (mole %) | |
|---|---|---|---|---|---|
| | | | Selec-tivity | N-Alkyl-aniline | N-Alkyl-formanilide |
| 3 | Methyl | 56.2 | 97.0 | 70.4 | 5.2 |
| 4 | Ethyl | 45.4 | 93.5 | 58.2 | 4.8 |
| 5 | Isopropyl | 48.2 | 97.2 | 62.4 | 5.6 |
| 6 | n-Butyl | 38.0 | 95.3 | 52.5 | 7.5 |

Notes:
(1) The yield of piperonal is expressed in terms of mole percentage based on the amount of N-alkylformanilide used.
(2) The selectivity of piperonal is expressed in terms of mole percentage based on the amount of 1,2-methylenedioxybenzene having reacted.

EXAMPLE 7

The procedure of Example 1 was repeated, except that phosphorus oxybromide was used in place of the phosgene. The results obtained are summarized in Table II.

EXAMPLE 8

The procedure of Example 2 was repeated, except that the phosgene was introduced at 70° C. over a 0.5-hour period, and, subsequently, the reaction mixture was kept at that temperature for 3 hours. The results obtained are summarized in Table II.

EXAMPLE 9

The procedure of Example 2 was repeated, except that thionyl chloride was used in place of the phosgene and that the reaction was carried out under a reduced pressure of 60–80 mmHg. The results obtained are summarised in Table II.

EXAMPLE 10

To 108 g (0.80 mole) of N-methylformanilide cooled in an ice-water bath, 95.2 g (0.80 mole) of thionyl chloride was added drop by drop with stirring. After completion of the addition, the mixture was allowed to stand it room temperature for 2 hours and then heated at 40°–50° C. for 1 hour under a reduced pressure of 60–80 nmHg. To the resulting yellow mixture, 97.6 g (0.80 mole) of 1,2-methylenedioxybenzene was added and kept at 15° C. Thereafter, the reaction with 1,2-methylenedioxybenzene was carried out in the same manner as in Example 1. The results obtained are summarized in Table II.

EXAMPLE 11

To the yellow mixture obtained according to the procedure of Example 10, 15 g of o-dichlorobenzene was added in place of the 1,2-methylenedioxybenzene. Thereafter, the reaction with 1,2-methylenedioxybenzene was carried out in the same manner as in Example 1, except that 122 g (1.0 mole) of 1,2-methylenedioxybenzene was charged into the other reactor. The results obtained are summarized in Table II.

EXAMPLE 12

The procedure of Example 10 was repeated, except that thionyl bromide was used in place of the thionyl chloride. The results obtained are summarized in Table II.

EXAMPLE 13

The procedure of Example 10 was repeated, except that sulfuryl chloride was used in place of the thionyl chloride. The results obtained are summarized in Table II.

EXAMPLE 14

The procedure of Example 10 was repeated, except that N-ethylformanilide was used in place of the N-methylformanilide. The results obtained are summarized in Table II.

Table II

| Example | R Group in N-Alkyl-formanilide | Condensing Agent | Piperonal (mole %) Yield | Selectivity | Recovery (mole %) N-Alkyl-aniline | A-Alkyl-formanilide |
|---|---|---|---|---|---|---|
| 7 | Methyl | Phosphorus oxybromide | 57.3 | 99.7 | 71.0 | 6.4 |
| 8 | " | Phosgene | 40.5 | 92.5 | 57.2 | 1.5 |
| 9 | " | Thionyl chloride | 47.2 | 88.5 | 62.0 | 3.5 |
| 10 | " | " | 55.6 | 95.1 | 70.5 | 4.2 |
| 11 | " | " | 53.7 | 93.8 | 71.0 | 3.4 |
| 12 | " | Thionyl bromide | 51.6 | 90.3 | 68.4 | 1.3 |
| 13 | " | Sulfuryl chloride | 34.2 | 83.2 | 53.6 | 2.7 |
| 14 | Ethyl | Sulfuryl bromide | 49.3 | 94.2 | 60.3 | 2.8 |

Notes:
1) The yield of piperonal is expressed in terms of mole percentage based on the amount of N-alkylformanilide used.
2) The selectivity of piperonal is expressed in terms of mole percentage based on the amount of 1,2-methylenedioxybenzene having reacted.

What is claimed is:
1. A process for preparing piperonal which comprises the steps of reacting 1,2-methylenedioxybenzene with an N-alkylformanilide of the general formula

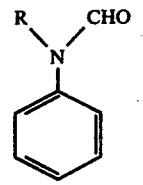

wherein R is an alkyl group having from 1 to 4 carbon atoms, and a condensing agent of at least one compound selected from the group consisting of phosgene, thionyl chloride, thionyl bromide, sulfuryl chloride, sulfuryl bromide, phosphorus trichloride, and phosphorus pentachloride, and then hydrolyzing the resulting reaction product to form piperonal.

2. A process as claimed in claim 1 wherein said 1,2-methylenedioxybenzene is reacted with said N-alkylformanilide and said condensing agent in the presence of an inert organic solvent.

3. A process as claimed in claim 1 wherein said N-alkylformanilide is N-methylformanilide or N-ethylformanilide.

4. A process as claimed in claim 1 wherein said condensing agent is phosgene.

5. A process as claimed in claim 1 wherein said condensing agent is added to a mixture of said 1,2-methylenedioxybenzene and said N-alkylformanilide at a temperature in the range of 50° to 100° C. and the reaction is carried out at the same temperature at which said condensing agent is added.

6. A process as claimed in claim 1 wherein said condensing agent is added to a mixture of said 1,2-methylenedioxybenzene and said N-alkylformanilide at a temperature in the range of −40° to 100° C. and, thereafter, the reaction is carried out at a temperature in the range of 50° to 110° C.

7. A process as claimed in claim 1 wherein said condensing agent comprises thionyl chloride, thionyl bromide, sulfuryl chloride, or sulfuryl bromide and wherein the reaction is carried out under a reduced pressure in the range of 20 to 400 mmHg.

8. A process for preparing piperonal which comprises the steps of reacting an N-alkylformanilide of the general formula

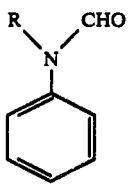

wherein R is an alkyl group having from 1 to 4 carbon atoms, with a condensing agent of at least one compound selected from the group consisting of phosgene, phosphorus oxychloride, phosphorus oxybromide, thionyl chloride, thionyl bromide, sulfuryl chloride, phosphorus trichloride, phosphorus pentachloride, and sulfuryl bromide, at a temperature in the range of $-40°$ to $100°$ C. to form a reaction mixture containing an amide chloride, adding the reaction mixture to 1,2-methylenedioxybenzene to react said amide chloride with said 1,2-methylenedioxybenzene at a temperature in the range of $50°$ to $120°$ C., and then hydrolyzing the resulting reaction product to form piperonal.

9. A process as claimed in claim 8 wherein said N-alkylformanilide is reacted with said condensing agent in the presence of 1,2-methylenedioxybenzene or an inert organic solvent.

10. A process as claimed in claim 9 wherein said inert organic solvent is benzene, chlorobenzene, o-dichlorbenzene, chloroform, carbon tetrachloride, methylene chloride, 1,2-dichloroethane, or trichloroethylene.

11. A process as claimed in claim 8 wherein said N-alkylformanilide is N-methylformanilide or N-ethylformanilide.

12. A process as claimed in claim 8 wherein said condensing agent is phosgene.

13. A process as claimed in claim 8 wherein said condensing agent comprises thionyl chloride, thionyl bromide, sulfuryl chloride, or sulfuryl bromide and wherein the reaction of said N-alkylformanilide with said condensing agent is carried out in the absence of any solvent, at a temperature in the range of $0°$ to $80°$ C., and under a reduced pressure in the range of 20 to 400 mmHg.

14. A process as claimed in claim 8, wherein said 1,2-methylene-dioxybenzene is mixed with an inert organic solvent.

15. A process for preparing piperonal which comprises the steps of reacting an N-alkylformanilide of the general formula

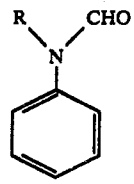

wherein R is an alkyl group having from 1 to 4 carbon atoms, with a condensing agent of at least one compound selected from the group consisting of phosgene, phosphorus oxychloride, phosphorus oxybromide, thionyl chloride, thionyl bromide, sulfuryl chloride, sulfuryl bromide, phosphorus trichloride and phosphorus pentachloride at a temperature in the range of $-20°$ to $70°$ C. to form a reaction mixture containing an amide chloride, adding the reaction mixture to 1,2-methylenedioxybenzene, and reaction mixture being kept at a temperature of from $-20°$ to $50°$ C. during the addition thereof, and said 1,2-methylenedioxybenzene being kept at a temperature of from $60°$ to $100°$ C. during the addition of said reaction mixture, heating the resulting mixture at a temperature of $60°$ to $100°$ C. to complete the reaction of said amide chloride with said 1,2-methylenedioxybenzene, and then hydrolyzing the resulting product to form piperonal.

16. A process as claimed in claim 15, wherein said N-alkylformanilide is N-methylformanilide or N-ethylformanilide.

17. A process as claimed in claim 15, wherein said condensing agent is phosgene.

* * * * *